(12) United States Patent
Huang et al.

(10) Patent No.: US 7,061,613 B1
(45) Date of Patent: Jun. 13, 2006

(54) POLARIZING BEAM SPLITTER AND DUAL DETECTOR CALIBRATION OF METROLOGY DEVICE HAVING A SPATIAL PHASE MODULATION

(75) Inventors: Chunsheng Huang, San Jose, CA (US); Pablo I. Rovira, San Francisco, CA (US); Jaime Poris, Boulder Creek, CA (US)

(73) Assignee: Nanometrics Incorporated, Milpitas, CA (US)

( * ) Notice: Subject to any disclaimer, the term of this patent is extended or adjusted under 35 U.S.C. 154(b) by 156 days.

(21) Appl. No.: 10/758,619

(22) Filed: Jan. 13, 2004

(51) Int. Cl.
*G01J 4/00* (2006.01)
(52) U.S. Cl. .................................................. 356/364
(58) Field of Classification Search ........ 356/364–370; 250/225
See application file for complete search history.

(56) References Cited

U.S. PATENT DOCUMENTS

| | | | |
|---|---|---|---|
| 4,298,283 A | 11/1981 | Makosch et al. | 356/495 |
| 4,583,855 A | 4/1986 | Baraket | 356/491 |
| 4,859,017 A | 8/1989 | Brierley et al. | 385/27 |
| 4,872,755 A | 10/1989 | Kuchel | 356/495 |
| 4,904,085 A * | 2/1990 | Spillman, Jr. et al. | 356/364 |
| 5,392,116 A | 2/1995 | Makosch | 356/351 |
| 5,502,567 A | 3/1996 | Pokrowsky | 356/367 |
| 5,561,525 A | 10/1996 | Toyonga et al. | 356/512 |
| 5,754,296 A | 5/1998 | Law | 356/369 |
| 5,889,593 A | 3/1999 | Bareket | 356/445 |
| 6,002,477 A | 12/1999 | Hammer | 356/307 |
| 6,052,188 A | 4/2000 | Fluckiger et al. | 356/369 |
| 6,122,052 A | 9/2000 | Barnes et al. | 356/328 |
| 6,160,621 A | 12/2000 | Perry et al. | 356/381 |
| 6,201,609 B1 | 3/2001 | Hill et al. | 356/491 |
| 6,275,291 B1 | 8/2001 | Abraham et al. | 356/367 |
| 6,297,880 B1 * | 10/2001 | Rosencwaig et al. | 356/369 |
| 6,304,330 B1 | 10/2001 | Millerd et al. | 356/521 |
| 6,452,682 B1 | 9/2002 | Hill et al. | 356/493 |
| 6,515,745 B1 | 2/2003 | Vurens et al. | 356/369 |
| 2002/0186373 A1 * | 12/2002 | Thoma et al. | 356/369 |
| 2003/0020912 A1 | 1/2003 | Norton et al. | 356/369 |

FOREIGN PATENT DOCUMENTS

| | | |
|---|---|---|
| EP | 0 987 537 A2 | 3/2000 |
| WO | WO 02/15238 A2 | 2/2002 |
| WO | WO 02/16893 A2 | 2/2002 |

OTHER PUBLICATIONS

Azzam, R.M.A. et al., *Ellipsometry and Polarized Light*, Chapter 3, "Theory and Analysis of Measurements in Ellipsometer Systems" (1987) pp. 167-268.

(Continued)

*Primary Examiner*—Gregory J Toatley, Jr.
*Assistant Examiner*—Isiaka O. Akanbi
(74) *Attorney, Agent, or Firm*—Silicon Valley Patent Group LLP

(57) ABSTRACT

An ellipsometer with a variable retarder, which introduces a spatial dependence in the beam, includes a polarizing beam splitter to produce two beams with orthogonal polarization states. The beam splitter may be, e.g., a polarizing displacer or polarizing beam splitter. The intensities of the two beams are measured, e.g., using separate detectors or separate detector elements in an array. The intensity from the two beams may be summed and used as a reference to normalize intensity of the produced beam.

24 Claims, 9 Drawing Sheets

OTHER PUBLICATIONS

Azzram, R., "An arrangement of two reflective photodetectors for measuring all four Strikes parameters of light", *American Institute of Physics* (1991) pp. 2080-2082.

Bennett, J., "Polarizers", Chapter 3, *Handbook of Optics*, (1995) pp. 3.1-.3.70.

Cumming, D. et al., "A variable polarization compensator using artificial dielectrics" Elsevier Science (1999) pp. 164-168.

Hauge, P., "Recent Developments in Instrumentation in Ellipsometry", *Surface Science* 96 (1980) pp. 108-140.

Horn, T., "Liquid Crystal Imaging Stokes Polarimeter", *Astronomical Society of the Pacific* (1999) pp. 33-37.

Jasperson, S., "A Modulated Ellipsometer for Studying Thin Film Optical Properties and Surface Dynamics" *Surface Science* 37 (1973) pp. 548-558.

Kazam, A. et al., "Compact and high-speed ellipsometer" *SPIE* vol. 1681 pp. (1992) 183-188.

Lee, J. et al., "Rotating-compensator multichannel ellipsometry: Applications for real time Stokes vector spectroscopy of thin film growth", *Review of Scientific Instruments* 69 (1998) pp. 1800-1810.

Oliva, E., "Wedged double Wollaston, a device for single shot polarimetric measurements", *Astronomy & astrophysics Supplement Series* 123 (1997) Pates 589-592.

Smajkjewicz, A., "An Argument for a Filter Array vs. Linear variable Filter in Precision Analytical Instrument Applications", Document #P95081.

"Stokes Polarimetry Using Liquid-Crystal Variable Retarders", downloaded Jun. 11, 2001 from http://www.meadowlark.com/ApppNotes/appnote3.htm, Meadowlark Optics, Inc. (1998-2001).

* cited by examiner

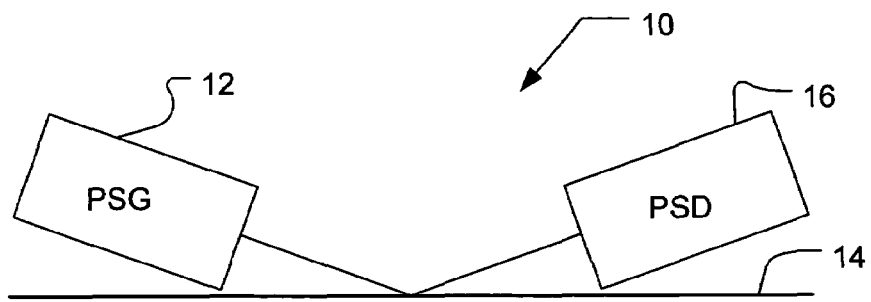
Fig. 1
(Conventional)
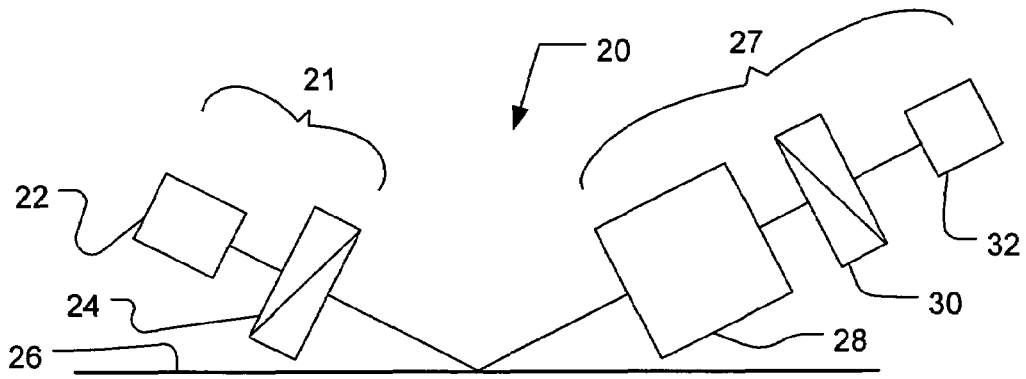
Fig. 2
(Conventional)

POLARIZING BEAM SPLITTER AND DUAL DETECTOR CALIBRATION OF METROLOGY DEVICE HAVING A SPATIAL PHASE MODULATION

CROSS-REFERENCE TO RELATED APPLICATION

This application is a related to U.S. patent application Ser. No. 09/929,625, filed Aug. 13, 2001, entitled "Metrology Device and Method Using a Spatial Variable Phase Retarder", which is incorporated herein by reference.

FIELD OF THE INVENTION

The present invention is related to optical metrology and in particular to a metrology device and technique that uses a spatially dependent phase shift as a component of an ellipsometer.

BACKGROUND

There is always a need for precise and reliable metrology to monitor the properties of thin films, especially in the semiconductor and magnetic head industries. Thin film properties of interest include the thickness of one or more layers, the surface roughness, the interface roughness between different layers, the optical properties of the different layers, the compositional properties of the different layers and the compositional uniformity of the film stack. Ellipsometers are particularly well suited to this task when the thickness is less than 100 nm, when there are more than two layers present or when there are compositional variations. Additionally, dimensional measurements such as linewidth, sidewall angle and height can be extracted using ellipsometry.

An ellipsometer is a measurement tool used to determine the change in polarization state of an electromagnetic wave after interaction with a sample. The determination of this polarization state can yield information about the thin film properties such as those listed above. In general, an ellipsometer is a polarization-state-in, polarization-state-out device. FIG. 1 shows a simple block diagram of a typical ellipsometer 10, which includes a Polarization State Generator (PSG) 12 that generates an electromagnetic wave of a known polarization state and a Polarization State Detector (PSD) 16 that determines the polarization state of the electromagnetic wave after interaction with a sample 14. In FIG. 1 the interaction is shown in reflection mode, but it should be understood that the interaction may be in transmission mode, i.e., the PSD determines the polarization state of the electromagnetic wave after transmission through a sample.

Different kinds of PSG/PSD configurations have been proposed and developed for ellipsometers. The advantages of each configuration are specific to the kind of extracted information that is desired. In the thin film metrology field, the most popular ellipsometry configurations include a rotating polarizing element. In these systems, the PSG and/or the PSD contain a rotating polarizing element utilizing a polarizer or compensator.

Unfortunately, rotating element configurations require moving parts employing motors, and therefore are more difficult to design into a compact tool. Compactness is a necessity for an application where the metrology module is integrated into a semiconductor process tool. Furthermore, moving components require maintenance and calibration and may degrade the reliability of the metrology tool.

Another kind of ellipsometer that has been extensively developed and used for thin film metrology is the photoelastic modulator ellipsometer (PME). This instrument employs a photoelastic modulator (PM) to change the polarization state of the light as a function of time either before or after reflection from the sample surface. This modulation can also be accomplished using a Pockels cell or liquid crystal variable retarders instead of a PM. One advantage of the PME is the lack of moving parts as the polarization is manipulated electrically.

FIG. 2 is a block diagram of a conventional PME 20. The PSG portion 21 of the PME 20 includes a light source 22 and a linear polarizer 24. The light source 22 generates a collimated beam (monochromatic or broadband radiation) that is transmitted through the linear polarizer 24. The linearly polarized beam is reflected from the sample surface 26 thereby modifying the polarization state of the electromagnetic beam. The PSD portion 27 of the PME 20 includes a PM (or Pockels cell) 28, another linear polarizer 30, and a detector 32. The PM (or Pockels cell) 28 introduces a time-dependent phase between the x- and y-electric field components of the reflected beam in relation to the optical axis of the PM 28. The linear polarizer 30 modulates the intensity of the incoming beam as a function of the phase imposed by the PM, which is a function of time. The detector 32 records the time-dependent intensity of the electromagnetic beam. The detector 32 can be a single element detector for a single wavelength system or a multichannel spectrograph when multiple wavelengths are used. Other configurations of a PME include a single PM in the PSG instead of the PSD, or a PM in both the PSG and the PSD.

Unfortunately, photoelastic modulators and Pockels cells are relatively large and expensive. Consequently, a disadvantage of an ellipsometer configuration employing modulated polarization such as shown in FIG. 2, is the larger size and greater cost relative to an ellipsometer that does not employ modulated polarization.

U.S. patent application Ser. No. 09/929,625, filed Aug. 13, 2001, entitled "Metrology Device and Method Using a Spatial Variable Phase Retarder", which is incorporated herein by reference described a metrology configuration that advantageously does not use moving parts or a phase modulator to measure a sample. Calibration of the system, however, requires a periodic reference measurement to minimize the effects of intensity variation due to non-uniformity of beam in phase modulation direction and illumination source, thermal and mechanical drift, which can be time consuming. Moreover, optical components of the system, e.g., the variable retarder, are moved out of the beam path during the reference measurement. Thus, there is a need for an improved system in which calibration reference data that can be easily and quickly measured.

SUMMARY

In accordance with an embodiment of the present invention, a metrology device with a variable retarder, which introduces a spatial dependence in the beam, includes a beam splitter to produce two beams with orthogonal polarization states. The beam splitter may be, e.g., a displacer or polarizing beam splitter. The intensities of the two beams are measured, e.g., using separate detectors or separate detector elements in an array. The intensity from the two beams may be summed and used as calibration reference data.

Accordingly, in one aspect of the present invention, a metrology device includes a polarization state generator that includes an electromagnetic source, the polarization state generator produces an electromagnetic beam of known polarization state that is incident on a sample. The metrology device includes a spatial variable phase retarder in the path of the electromagnetic beam after the sample and a polarizing beam splitter in the path of the electromagnetic beam after the spatial variable phase retarder. The polarizing beam splitter splits the beam into a first beam having a first polarization state and a second beam having a second polarization state that is orthogonal to the first polarization state. A first set of detector elements are within the path of the first beam after the polarizing beam splitter and a second set of detector elements are within the path of the second beam after the polarizing beam splitter. The first set of detector elements and the second set of detector elements measure the intensity of the first beam and second beam, respectively, as a function of position. In one embodiment, the metrology device may include a computer system coupled to the first set of detector elements and second set of detector elements, the computer system receiving signals indicative of the intensity of the first beam and the second beam, the computer system having a computer-usable medium having computer-readable program code embodied therein for summing the intensities of the first beam and the second beam. The intensity of the first beam or second beam can be normalized by the summed intensity.

Another aspect of the present invention includes a method of ellipsometrically measuring a sample. The method includes producing a light beam of known polarization state that is incident on a sample. The method further includes creating a spatially dependent relative phase difference between the electromagnetic field components of the beam. The beam is then split to produce two beams having orthogonal polarization states and the intensities of the two beams at a plurality of positions. In one embodiment, the intensities are summed and may be used as a reference, e.g., to normalize the spatially phase modulated beam intensity.

In yet another aspect of the present invention, an apparatus for measuring a characteristic of a sample includes a light source that produces an electromagnetic beam, a polarizer in the path of the electromagnetic beam, wherein the polarized electromagnetic beam is incident on the sample. The apparatus includes a means for producing a spatially dependent phase shift in the electromagnetic beam after the electromagnetic beam is incident on the sample. The means for producing a spatially dependent phase shift produces a spatially phase modulated beam. The apparatus further includes a means for splitting the phase shifted beam into a first beam and a second beam, wherein the first beam and second beam are orthogonally polarized and a means for measuring the intensity of the first beam and the second beam, the means for measuring being in the path of the first beam and the second beam. The apparatus further includes a means for summing the intensities of the first beam and the second beam.

BRIEF DESCRIPTION OF THE DRAWINGS

FIG. 1 shows a simple block diagram view of a typical ellipsometer including a Polarization State Generator (PSG), a sample and a Polarization State Detector (PSD).

FIG. 2 is a block diagram of a conventional photoelastic modulator ellipsometer (PME).

DETAILED DESCRIPTION

Figure 3:
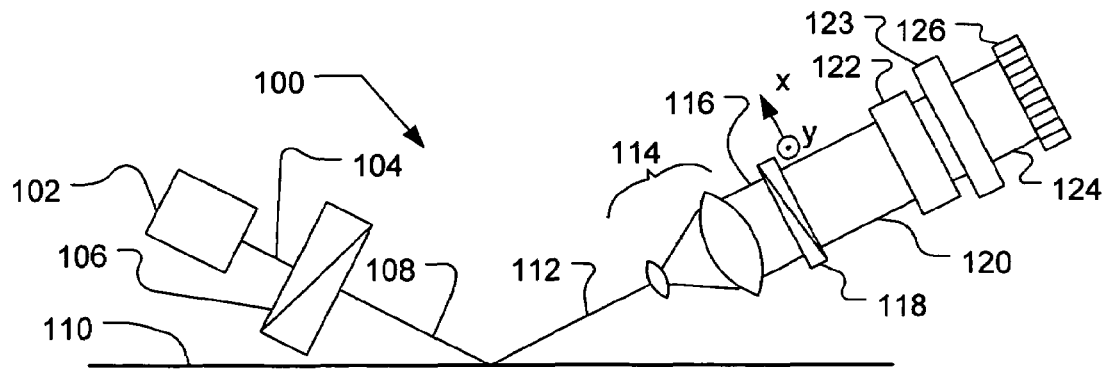
FIG. 3 is a block diagram of an ellipsometer with no moving parts and no phase modulator in accordance with an embodiment of the present invention.

In accordance with an embodiment of the present invention, a metrology device, such as an ellipsometer, has no moving parts and no temporal phase modulator. Such a metrology device is described in U.S. patent application Ser. No. 09/929,625, filed Aug. 13, 2001, entitled "Metrology Device and Method Using a Spatial Variable Phase Retarder", which is incorporated herein by reference. FIG. 3 shows a block diagram of an ellipsometer 100 in accordance with an embodiment of the present invention. After the light beam of known polarization state is reflected from the sample 110, the beam is expanded and passed through a variable retarder 118 to introduce a spatially dependent phase shift. The expanded beam then passes through a polarizer and the intensity is measured using multi-element detector 126. Ellipsometer 100 may be used advantageously for semiconductor thin film applications. Due to its small size, it may be integrated into various semiconductor processor tools.

As shown in FIG. 3, ellipsometer 100 includes an electromagnetic source 102 that generates a collimated beam 104 of monochromatic or broadband radiation that is transmitted through polarizer 106 to produce a polarized beam 108. The polarized beam 108 is incident on and interacts with the sample surface 110 to produce a reflected beam 112. Reflected beam 112 has a modified polarization state compared to polarized beam 108. It should be understood that if desired, ellipsometer 100 may operate in transmission mode in which case the beam passes through the sample. For the sake of simplicity, the present disclosure will describe ellipsometer in reflection mode using a reflected beam, with the understanding that a transmitted beam may alternatively be used.

After reflection from the sample surface 110, the reflected beam 112 is expanded in the plane of the drawing (the x direction) by expander 114 to produce expanded beam 116. It should be understood, however, that beam expander 114 is used to shape the beam so that it adequately fills the variable retarder 118 and a multi-element detector 126 with the reflected signal. If the beam adequately fills the variable retarder 118 and multi-element detector 126, e.g., if electromagnetic source 102 produces the properly shaped beam, beam expander 114 is unnecessary.

The expanded beam 116 is then transmitted through a variable retarder 118 whose geometry is matched to the shape of the expanded beam. The variable retarder 118 has the property of creating a relative phase difference δ between the electric field components parallel (ordinary or o) and perpendicular (extraordinary or e) to the optical axis of the variable retarder 118 in the x direction. The resulting phase shifted beam 120 is then transmitted through a polarizer (linear polarizer) 122. A multi-element detector 126 then records the intensity of resulting beam 124. The detector geometry is chosen to match the geometry of the beam expander 114 and variable retarder 118. The multi-element detector 126 may be a photodiode array (PDA) or a multi-element charge coupled device (CCD).

It should be understood that if desired, the expander 114 and variable retarder 118 may be located in the PSG, i.e., before the sample surface 110. In this embodiment, for example, the expanded beam is focused onto the sample surface 110 and, e.g., a colliminator lens is added in place of the beam expander 114. The beam is collimated by the colliminator lens so that it matches the geometry of the detector 126. The polarizer 122 would still be located before the detector 126.

In a spectroscopic embodiment, broadband radiation is emitted from source 102. Additionally, the light beam must be expanded in the y direction, which will be described below. An additional optical component, such as an interferometric filter 123, is required to separate the various wavelengths of the beam. An appropriate interferometric filter 123 has a linear variation of the transmitted wavelength in the y direction. The filter 123 can also be made up of individual interferometric elements. Interferometric filters are composed of stacks of thin films with different thicknesses chosen such that essentially only one wavelength is transmitted through the filter. It is possible to construct an interferometric filter employing a gradient in thickness of the thin films in one direction such that a continuous spectrum of wavelength filters is obtained. These kinds of filters may be custom-manufactured by, e.g., Barr Associates, Inc. located in Westford, Mass. With the gradient oriented in the y direction and a multi-element detector 126 that has elements in the x and y directions, the detector 126 maps the intensity of the resulting beam as a function of retardance δ in the x direction and as a function of wavelength λ in the y direction. The intensities recorded by the detector 126 can then be analyzed to obtain the ellipsometry angles ψ and Δ as a function of wavelength.

The interferometric filter 123 is preferentially located immediately preceding the detector 126 to minimize adverse optical effects. It could also be located anywhere after the beam is expanded in the y direction before the detector 126.

Figure 4:
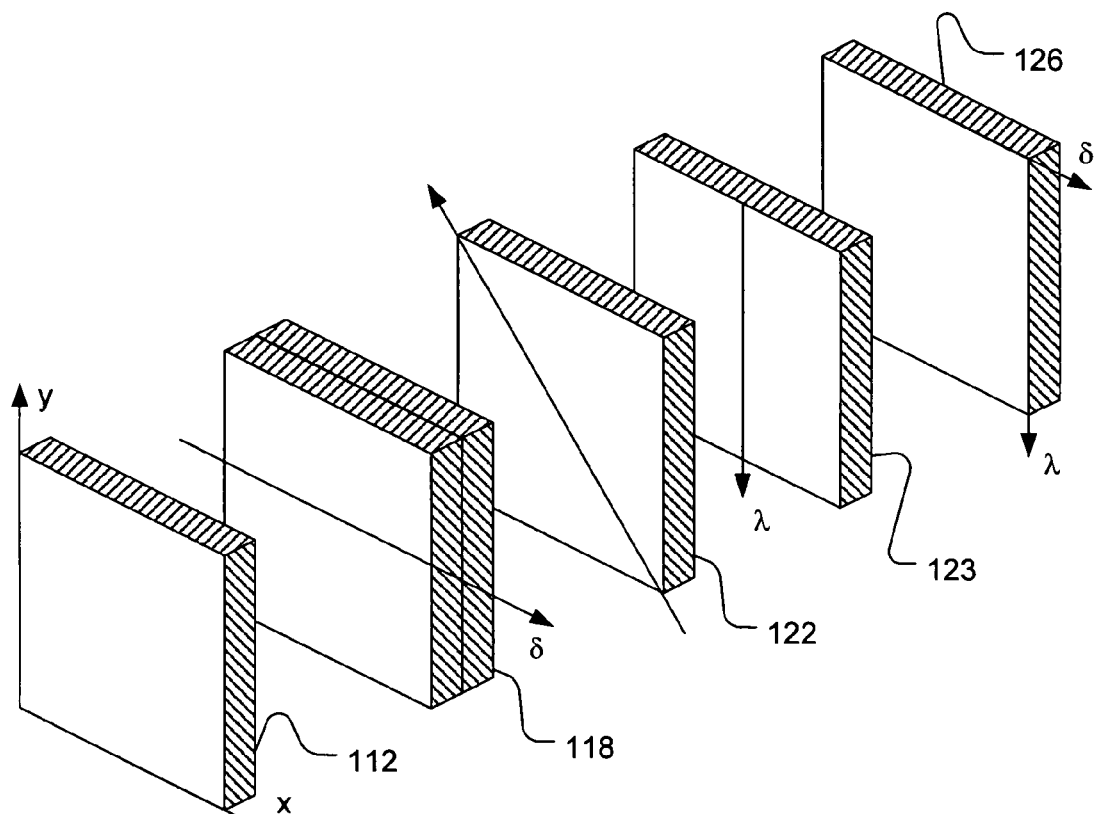
FIG. 4 shows a perspective view of the PSD from the ellipsometer in FIG. 3 when used in spectroscopic mode.

FIG. 4 shows a perspective view of the PSD after beam expansion in ellipsometer 100 in FIG. 3 where the expanded beam 112 is illustrated as plate 112 for the sake of simplicity. As shown in FIG. 4, spatial variable retarder 118 varies the phase δ along the x-axis and interferometric filter 123 varies the wavelength λ along the y-axis. The polarizer 122 creates the sinusoidal modulation of the intensity. Thus, as illustrated in FIG. 4, the detector 126 measures the intensity of the light beam as a function of phase δ along the x-axis and wavelength λ along the y-axis.

Figure 5:
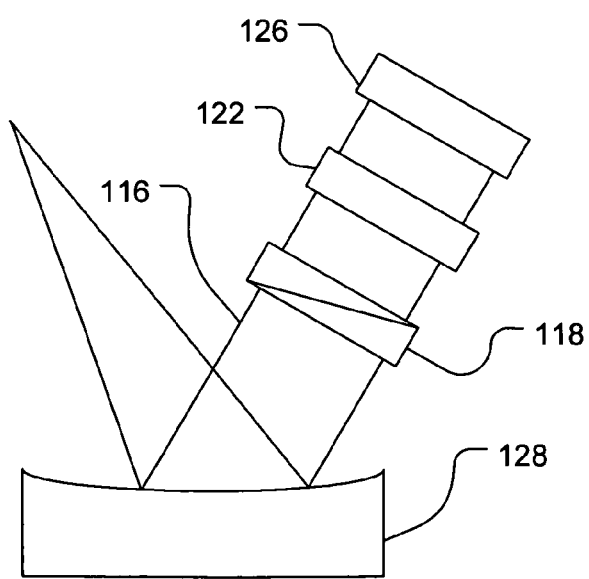
FIG. 5 shows a reflecting diffraction grating that expands and collimates the beam in the PSD.

Other hardware configurations can be devised for spectroscopic ellipsometry in accordance with the present invention. For example, as shown in FIG. 5, a reflecting diffraction grating 128 is used to collimate the beam in reflection in the x direction as well as separate the wavelengths in the signal by diffraction in the y direction. In this case, the reflecting diffraction grating 128 replaces the interferometric filter 123 shown in FIGS. 3 and 4 and the collimating components of the beam expanding optics 114 shown in FIG. 3. In this configuration, the reflecting diffraction grating 128 operates as part of the expander in the ellipsometer used to expand the reflected beam to fill the variable retarder 118. Transmission gratings can also be employed to spread the beam in the y direction.

Figure 6A:
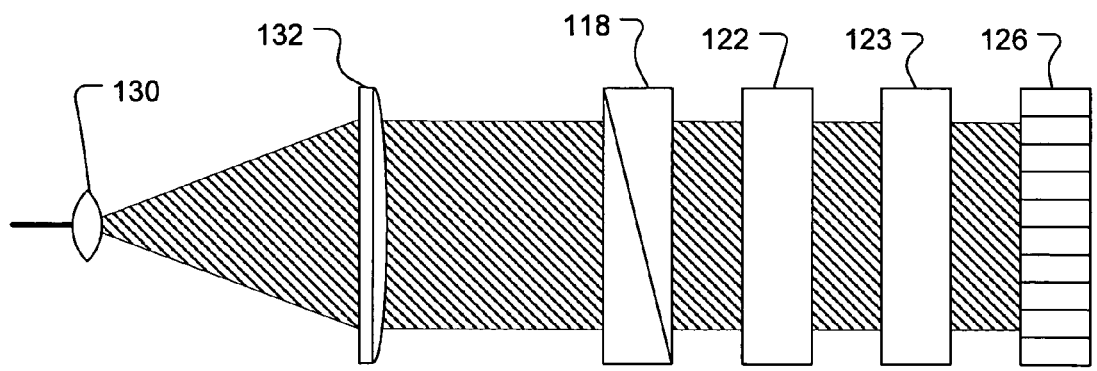
FIG. 6A shows a lens system to expand and collimate the beam to cover the entire PSD detector area.
Figure 6B:
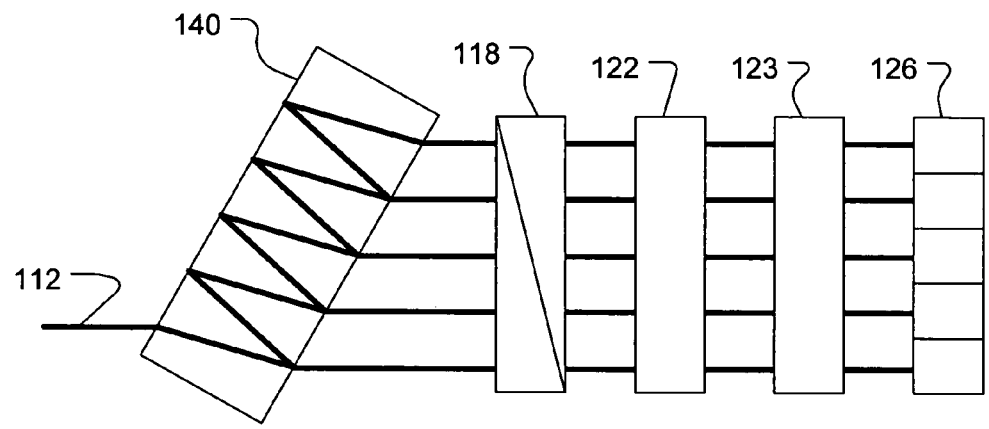
FIG. 6B shows an etalon that is used to spatially expand the reflected beam into several discrete beams to cover the entire PSD detector area.
Figure 6C:
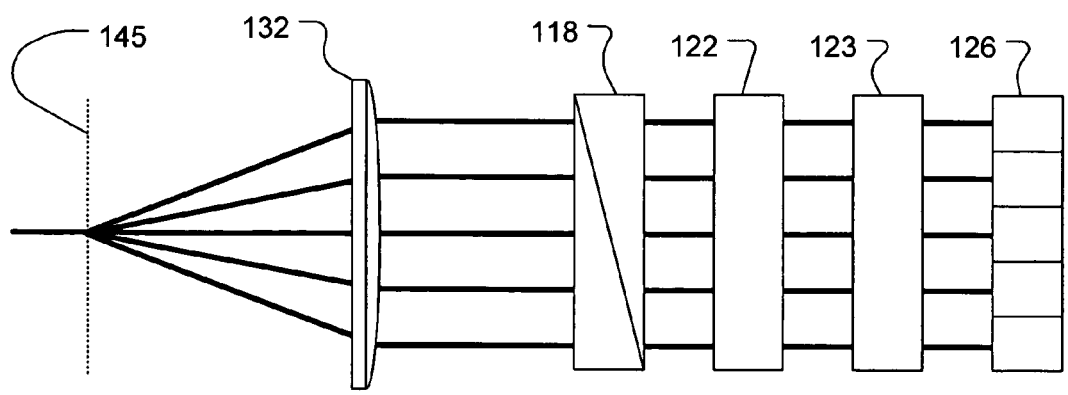
FIG. 6C shows transmission diffraction grating that is used to spatially expand the reflected beam to cover the entire PSD area.

Numerous techniques can be devised to expand the reflected beam 112 to fill the variable retarder 118 and detector 126. For example, as shown in FIG. 3 and in FIG. 6A, lenses 130 and 132 can be used to expand and collimate the reflected beam 112 to cover the desired PSD area. Alternatively, as shown in FIG. 6B, an etalon 140 can be used to divide the reflected beam 112 into a plurality of discrete beams to functionally spatially expand the beam. Multiple reflections inside the etalon 140 generate parallel beams of equal intensity from a properly coated etalon. The detector elements in detector 126 should then be aligned to the discrete beams produced by the etalon 140. Diffractive optics such as a grating 145 can also be used, along with collimating lens 132, to spatially expand the beam into a plurality of individual beams of equal intensity, as shown in FIG. 6C.

Figure 7A:
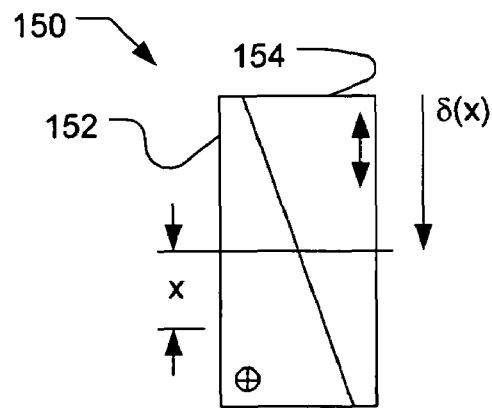
FIGS. 7A, 7B, and 7C show three embodiments of a variable retarder that may be used in the PSD shown in FIG. 3.
Figure 7B:
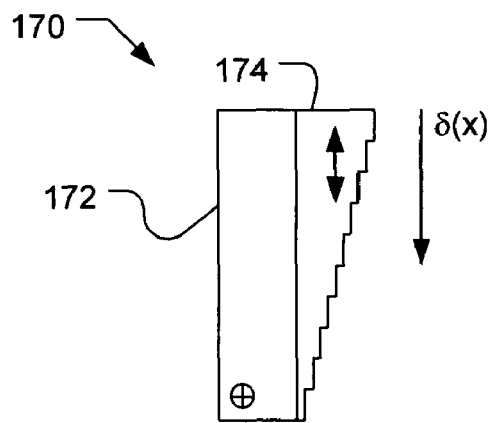
Figure 7C:
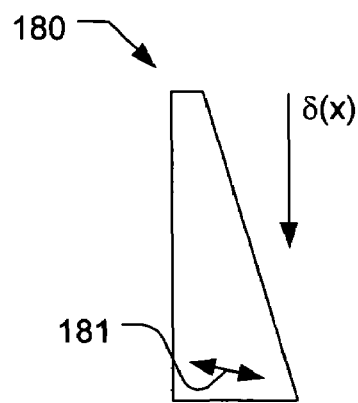

FIGS. 7A, 7B, and 7C show three illustrative variable retarders that may be used with the present invention. The variable retarder 150 shown in FIG. 7A, consists of two wedged plates 152 and 154 composed of birefringent material whose outer surfaces are orthogonal to the beam propagation direction. The optical axes of the plates 152 and 154 are perpendicular to each other. An example of variable retarder 150 is manufactured by InRad Inc. located at New Jersey. The effective retardance for variable retarder 150 assuming an orthogonal incident beam is given by:

$$\delta(x) = \frac{4\pi}{\lambda} \Delta n x \tan\Phi, \qquad \text{eq. 1}$$

where x is the distance from the center of the variable retarder 150, Δn is the birefringence (which is a function of wavelength λ), i.e., the difference between the ordinary and extraordinary refractive indexes assuming both wedges are made of the same material, and Φ is the wedge angle of the internal faces of the two birefringent plates 152 and 154. The angle Φ is preferably chosen so that the retardance δ varies over a range of at least 2π radians for the wavelengths of interest. An additional complexity is that the o and e beams start to diverge at the interface of the two wedges and continue to diverge at the exiting air interface. Therefore, Φ should be chosen as small as possible to minimize the separation between the two polarization components. As shown in FIG. 3, it is desirable to locate the detector 126 as close as possible to the variable retarder 118. Alternatively, a lens following the variable retarder 118 may be used to correct this divergence.

FIG. 7B shows another example of a variable retarder 170 composed of two plates. The first plate 172 has two parallel faces. The second plate 174 has one flat face and a second face with a series of steps of different thicknesses. If desired, the second plate 174 may have a continuously changing thickness rather than a series of steps. The optical axes of the first plate 172 and the second plate 174 are perpendicular to each other similar to the variable retarder 150 described in FIG. 7A. The relative phase difference δ is once again a function of position from the center of the plate. The steps in plate 174 could also be varied in thickness in the y direction for spectroscopic applications to maintain a constant phase delay for each wavelength. This configuration of a variable retarder does not result in a divergence of the two o and e components of the polarized beam. The variable retarder shown in FIG. 7B is also useful in an interferometer.

FIG. 7C is another example of a variable retarder 180 composed of a single wedge. Variable retarder 180 is a made up of a single plate of birefringent material with non-parallel faces. The optical axis must be at a very small angle (almost parallel) to the beam propagation direction as indicated by arrow 181. Thus, the optical axis is at an oblique angle with the direction of propagation of the electromagnetic beam. This geometry creates an effective birefringence given by the projection of the ordinary and extraordinary indices of refraction to the plane perpendicular to the direction of propagation.

It should be understood that other variable retarders could be used. For example, a liquid crystal array, where it is possible to control the birefringence of individual pixels in the x and y directions may be used, as described in T. Horn and A. Hofmann, "Liquid Crystal Imaging Stokes Polarimeter", ASP Conference Series Vol. 184, pp. 33–37 (1999), which is incorporated herein by reference. Moreover, a variable retarder that uses artificial dielectrics may be used, such as that described in D. R. S. Cumming and R. J. Blaikie, "A Variable Polarization Compensator Using Artificial Dielectrics", Opt. Commun. 163, pp. 164–168 (1999), which is incorporated herein by reference.

Figure 8:
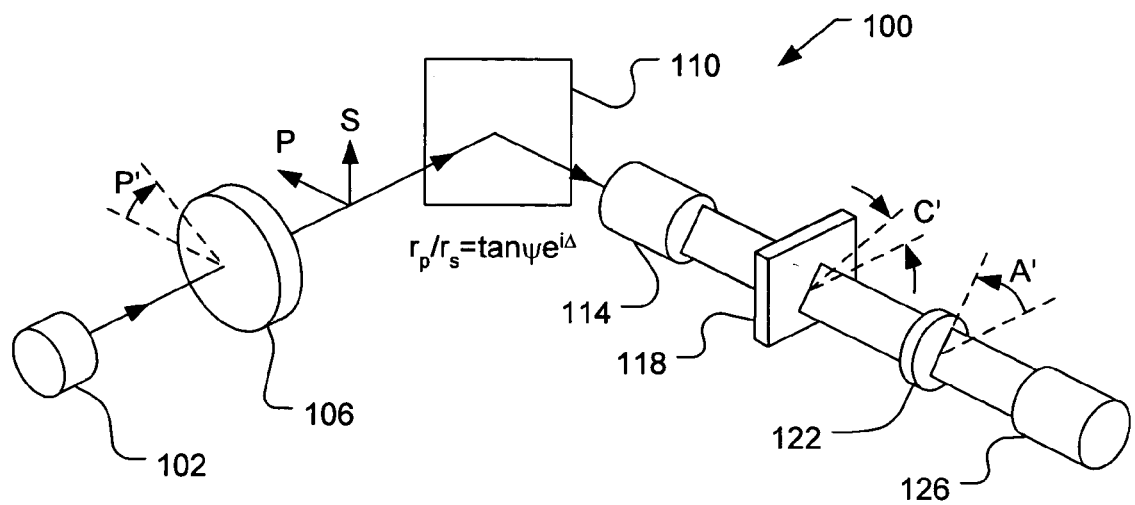
FIG. 8 shows a perspective view of an ellipsometer with no moving parts indicating the calibration parameters.

For the system shown in FIG. 3, the Mueller formalism can be used to yield the following dependence for the intensity as measured by the multi-element detector 126 as a function of δ(x):

$$I=I_0\{1+\sin 2(C'-A')\sin 2(C'-Q)\cos \delta(x)\cos 2\chi+\cos 2(C'-A')\cos 2(C'-Q)\cos 2\chi-\sin 2(C'-A')\sin \delta(x)\sin 2\chi\}$$ eq. 2 where $I_0$ is the intensity without polarization, C' is the angle of the optical axis of the variable retarder 118, and A' is the angle of the transmission axis of the polarizer 122. Both the C' and A' angles are measured with respect to the plane of incidence, as shown in FIG. 8, which shows a perspective view of ellipsometer 100. The retardance of the variable retarder 118 is represented in equation 2 by δ(x). The ellipticity angle is represented by χ and the tilt angle defining the polarization state of the reflected beam is represented by Q.

Figure 9:
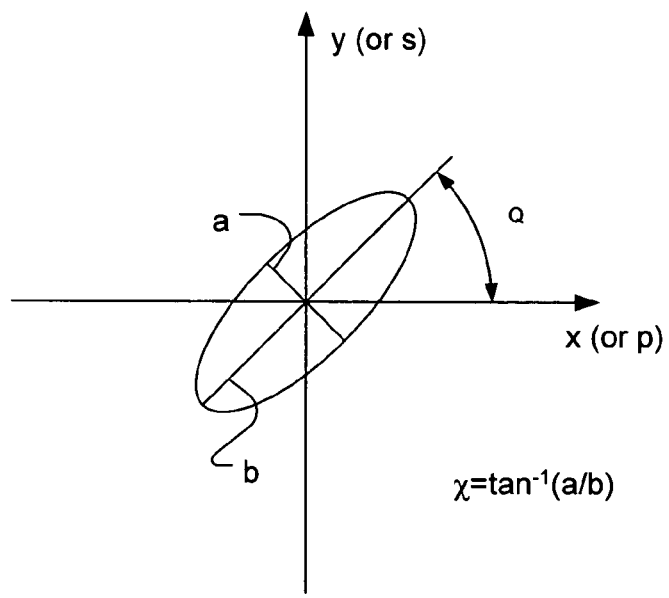
FIG. 9 shows a representation of the polarization state of an electromagnetic beam in terms of its ellipsometric angles $\chi$ and Q.

FIG. 9 is a representation of a polarization state of an electromagnetic beam in terms of its ellipsometry angles χ and Q, with the x-axis parallel to the plane of incidence. When Q is greater than zero, the angle is defined as counter-clockwise for an incoming beam, as shown in FIG. 9. The sign of χ determines the handedness of the polarization state, i.e., positive χ indicates left-handed rotation, whereas negative χ indicates right-handed rotation, also shown in FIG. 9.

The quantities χ and Q are related to the ellipsometry angles ψ and Δ by:

$$\cos 2\psi = \frac{\cos 2P' - \cos 2Q\cos 2\chi}{1 - \cos 2Q\cos 2\chi \cos 2P'}$$ eq. 3A $$\tan \Delta = -\frac{\tan 2\chi}{\sin 2Q}$$ eq. 3B where P' is the angle of the transmission axis of the polarizer 106 with respect to the plane of incidence, as shown in FIG. 8. Ellipsometry angles and equations 3A and 3B are described in more detail in Joungchel Lee, P. I. Rovira, Ilsin An, and R. W. Collins, "Rotating-Compensator Multichannel Ellipsometry: Applications for Real Time Stokes Vector Spectroscopy of Thin Film Growth", Rev. Sci. Intrum. 69, pp. 1800–1810 (1998), which is incorporated herein by reference. The ellipsometry angles ψ and Δ can then be modeled using, e.g., the Fresnel formalism to obtain the thin film properties of the sample.

In order to obtain χ and Q, the intensity given by equation 2 may be analyzed, e.g., using regression analysis, once the intensities of the multi-element detector 126 are measured. An additional approach shows the normalized intensity written as:

$$I'=1+\alpha \cos \delta + \beta \sin \delta$$ eq. 4

Where α and β are described by the following equations:

$$\alpha = \frac{\sin 2(C'-A')\sin 2(C'-Q)\cos 2\chi}{1+\cos 2(C'-A')\cos 2(C'-Q)\cos 2\chi}$$ eq. 5A $$\beta = \frac{-\sin 2(C'-A')\sin 2\chi}{1+\cos 2(C'-A')\cos 2(C'-Q)\cos 2\chi}.$$ eq. 5B One advantageous configuration of angles is P'=45°, C'=0°, and A'=−45°, but other configurations may be used.

Figure 10A:
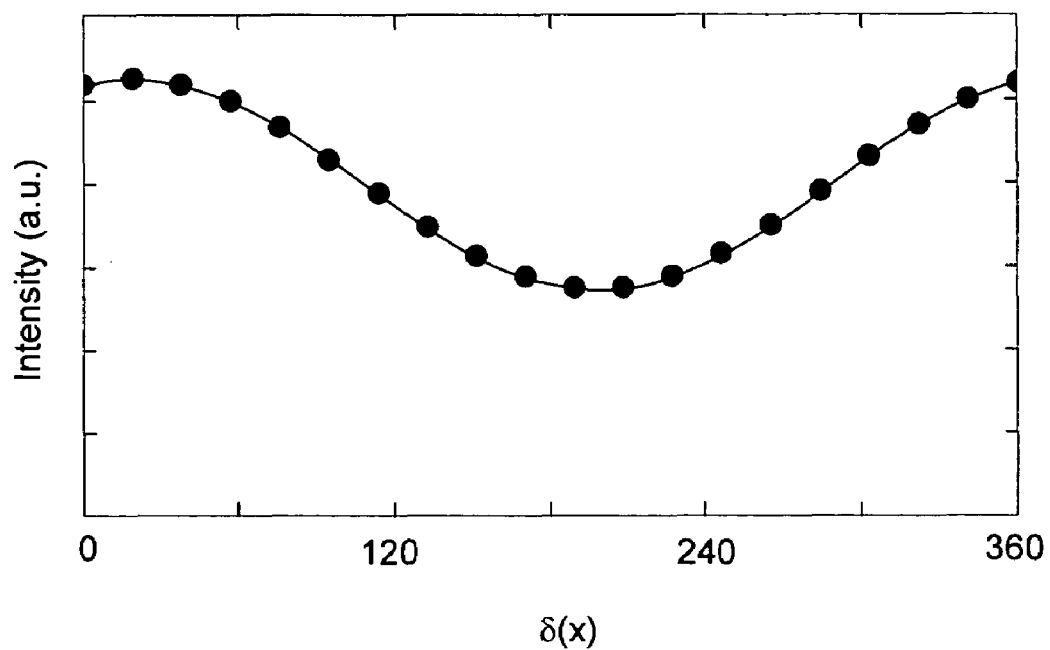
FIG. 10A shows the modulated intensity signal detected by the multi-element detector.

FIG. 10A shows the modulated intensity signal in arbitrary units detected by the multi-element detector 126. If the intensity is modulated by 2π radians and the photodetector array contains N detectors, as shown in FIG. 10A, the Fourier coefficients can be obtained from the following relations:

$$\alpha = \frac{1}{I_{sum}} \sum_{q=1}^{N} I_{\exp,q} \cos \delta_q,$$ eq. 6A

-continued $$\beta = \frac{1}{I_{sum}} \sum_{q=1}^{N} I_{exp,q} \sin\delta_q, \quad \text{eq. 6B}$$

$$I_{sum} = \sum_{q=1}^{N} I_{exp,q}. \quad \text{eq. 6C}$$

Figure 10B:
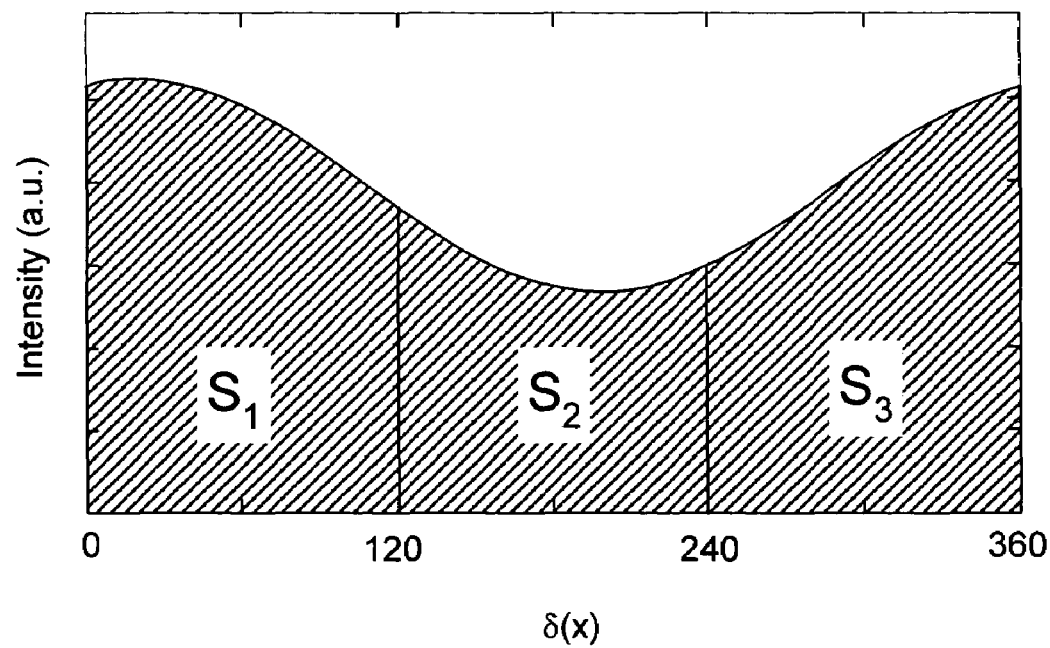
FIG. 10B shows the same modulated intensity detected by three detectors, which collect the partial integrals of the modulated intensity.

In an alternative approach, using a multi-element detector with a limited number of elements, the output of each element is proportional to the area of the intensity curve, as shown in FIG. 10B for the case of a three-element detector. This technique has the potential to improve the data collection throughput. In FIG. 10B, each element covers one third of the total modulation. Each detector will collect an intensity that is proportional to the partial integrals of I(x). The integrals of the intensity $S_j$ (j=1, 2, 3, . . . ) are referred to in the literature as Hadamard sums. Therefore, for the case of three detectors and a complete modulation period, the following can be written:

$$S_m = \int_{2\pi(m-1)/3}^{2\pi m/3} I_0[1 + \alpha\cos(\delta(x)) + \alpha\cos(\delta(x))] \, d\delta(x), \quad \text{eq. 7}$$

where m=1, 2, 3.
Thus:

$$S_1 = I_0\left(\frac{2}{3}\pi + \frac{\sqrt{3}}{2}\alpha + \frac{3}{2}\beta\right), \quad \text{eq. 8A}$$

$$S_2 = I_0\left(\frac{2}{3}\pi - \sqrt{3}\,\alpha\right), \quad \text{eq. 8B}$$

$$S_3 = I_0\left(\frac{2}{3}\pi + \frac{\sqrt{3}}{2}\alpha - \frac{3}{2}\beta\right). \quad \text{eq. 8C}$$

Inverting these equations, the normalized Fourier coefficients will be given by:

$$\alpha = \frac{2\pi}{3\sqrt{3}} \frac{(-S_1 + 2S_2 - S_3)}{(S_1 + S_2 + S_3)}, \quad \text{eq. 9A}$$

$$\beta = \frac{2\pi}{3} \frac{(S_1 - S_3)}{(S_1 + S_2 + S_3)}. \quad \text{eq. 9B}$$

Summarizing, in order to obtain the ellipsometry angles ψ and Δ associated with a thin film stack on a sample, the intensity as a function of detector position is first measured. The quantities Δ and β are calculated either from equations 6A–6C, or equations 9A–9B. Next, the angles χ and Q are calculated from equations 5A–5B after inversion. Finally, the ellipsometry angles ψ and Δ are obtained from equations 3A–3B.

The PSD of the ellipsometer 100 can also be used as a photopolarimeter, i.e., a beam of unknown polarization state (χ, Q) can be measured by the PSD. The collected intensity can then be analyzed to obtain (χ, Q), which defines the polarization state of the incoming beam as in FIG. 9.

In addition, it should be understood that PSD shown in FIG. 4 may be used with metrology instruments other than the ellipsometer shown in FIG. 3. For example, the polarization state detector of FIG. 4 may be used as a photopolarimeter. A photopolarimeter is used to analyze the polarization state of an electromagnetic beam. Photopolarimeters are used, e.g., in the telecommunication industry, as it is often desirable to know the polarization state of beams emanating from an optical fiber. Photopolarimeters are also used in an astrophysics application, in which the polarization state of solar electromagnetic radiation is analyzed.

Figure 11:
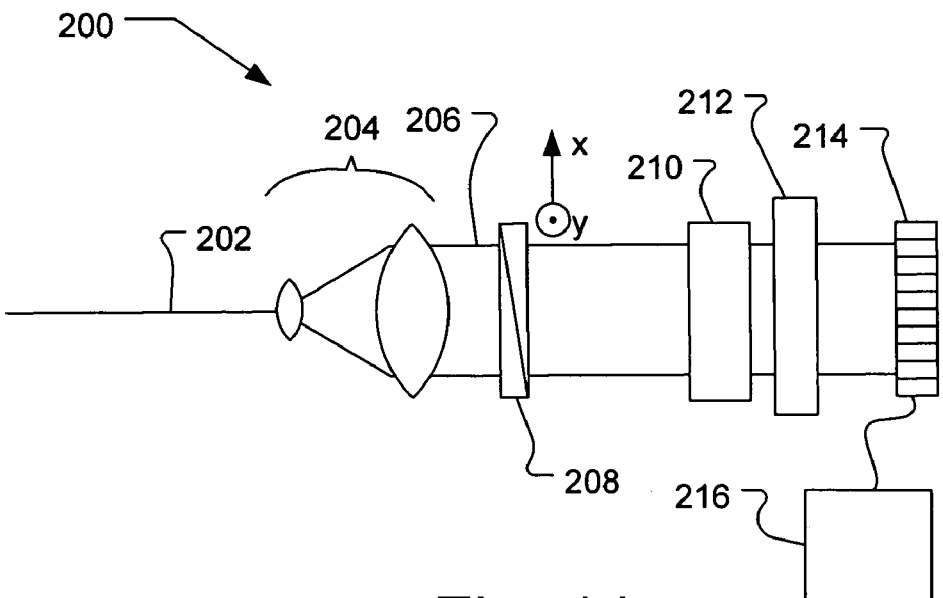
FIG. 11 is a block diagram of a photopolarimeter in accordance with an embodiment of the present invention.

The operation of a photopolarimeter 200, in accordance with an embodiment of the present invention, is described with reference to FIG. 11. An electromagnetic beam 202 that is received by the photopolarimeter 200 is orthogonally incident on the beam expander 204 if beam expansion is required. The expanded beam 205 is incident on the spatial variable retarder 208. If beam expansion is not required, i.e. the received electromagnetic beam 202 is already properly shaped to fill the variable retarder 208 and the detector 214, the beam expander 204 is unnecessary. After transmission through the variable retarder 208, the electromagnetic beam is then linearly polarized by polarizer 210 and collected by the multi-element detector 214. If the electromagnetic beam 202 to be analyzed consists of broadband radiation, the electromagnetic beam must also be expanded by interferometric filter 212 in the direction orthogonal to the phase variation direction imposed by the spatial variable retarder 208. Thus, for example, the spatial variable retarder 208 varies the phase along the x-axis and the interferometric filter 212 varies the wavelength along the y-axis. The data is then analyzed by a data processing machine 216 coupled to the multi-element detector 214 to yield the polarization state of the electromagnetic beam 202.

To obtain the polarization state of the electromagnetic beam 202 from the collected intensities from the multi-element detector 214, the data processing machine 216 implements software to calculate the Fourier coefficients α and β from equations 6A–6C or 9A–9B. The particular equations used depend on the detector configuration, as described above. Next, the data processing machine 216 implements software to calculate the tilt angle Q and ellipticity angle χ using equations 5A and 5B. As illustrated in FIG. 9, the angles Q and χ define the polarization state of the incoming electromagnetic beam 202. Software that may be implemented by data processing machine 216 to calculate the Fouirer coefficients Δ and β from equations 6A–6C or 9A–9B and the tilt angle Q and ellipticity angle χ from equations 5A and 5B may be written by one of ordinary skill in the art.

Figure 12:
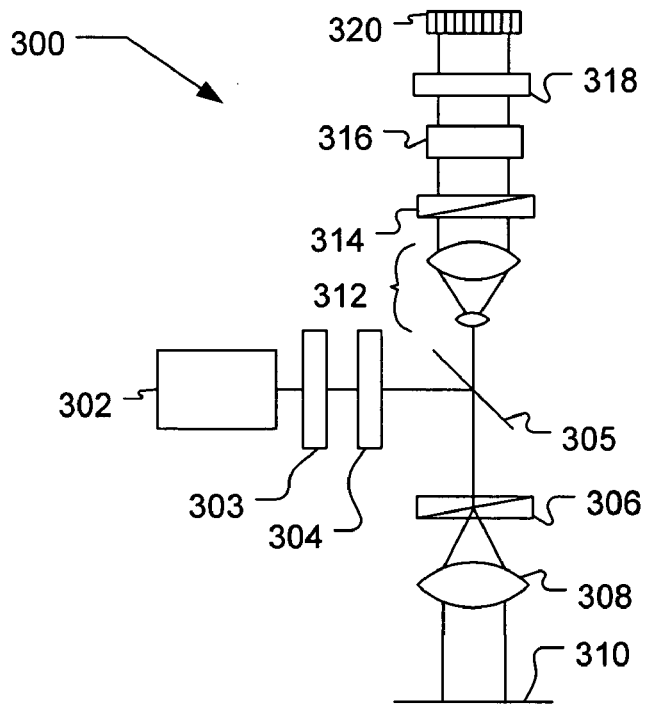
FIG. 12 is a block diagram of an interferometer in accordance with an embodiment of the present invention.

In addition, if desired, the PSD with or without a beam expander may be used in an interferometer 300, shown in FIG. 12. Interferometer 300 includes an electromagnetic source 302 followed by a half-wave plate 303 and a polarizer 304. A beam splitter 305 directs the electromagnetic beam towards the sample 310. A Wollaston prism 306 splits the light beam into two light beams, which are focused on the sample by lens 308. The two beams are reflected off sample 310 and travel back through lens 308 and prism 306, where the two beams are recombined into a single superimposed beam before passing through beam splitter 305. The beam is then expanded by beam expander 312 and passes through a spatial variable retarder 314. If the beam does not need expanding, as discussed above, beam expander 312 need not be used. The beam passes through a polarizer 316 and an interferometric filter 318 (if desired) prior to being received by multi-element detector 320. Thus, the multi-element detector 320 receives a single superimposed electromagnetic beam. The single beam received by detector 320 is appropriately shaped to fill the detector 320 by beam expander 312 (if beam expansion is necessary) or by other optical elements, e.g., lens 308, prism 306, beam splitter 305, or the light source 302 itself, (if beam expansion is not used). In addition, if desired, spatial variable retarder 314 may be a single plate of birefringent material with non-parallel faces, with the optical axis at a small angle (almost parallel) to the beam propagation direction, as discussed in FIG. 7C.

Figure 13:
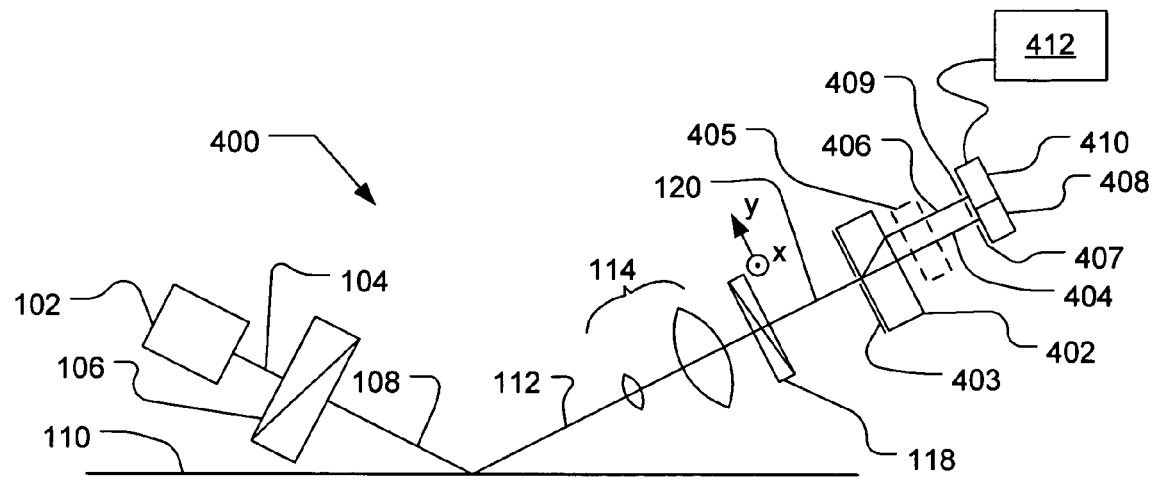
FIG. 13 is a block diagram of an ellipsometer, similar to that shown in FIG. 3, but with a beam splitter that beam after the variable retarder 118 into a two beams that are orthogonally polarized.

FIG. 13 shows an ellipsometer 400, in accordance with another embodiment of the present invention. Ellipsometer 400 is similar to ellipsometer 100 shown in FIG. 3, like numbered elements being the same. Ellipsometer 400, however, includes a beam splitter 402 that splits the beam after the variable retarder 118 into two beams 404 and 406 that have orthogonally orientated polarization states. For example, beam 404 may be an ordinary polarized beam 404 and an extraordinary polarized beam 406. Thus, the beam splitter 402 acts as a static analyzer and may replace the analyzer 122 of ellipsometer 100. The ordinary polarized beam 404 and the extraordinary polarized beam 406 are received by detectors 408 and 410.

It should be understood that after reflection from the sample surface 110, the reflected beam 112 is expanded in the plane orthogonal to the page (the x direction) by expander 114 to produce an expanded beam 116. It should be understood, however, that beam expander 114 is used to shape the beam so that it adequately fills the variable retarder 118 and the detectors 408 and 410 with the reflected signal.

Thus, the detectors 408 and 410 receive the ordinary polarized beam 404 and the extraordinary polarized beam 406. It should be understood that the detectors 408 and 410 may be physically separate linear detectors or may be an array of photodetecters, such as a CCD, that receives both beams 404 and 406. The CCD array can be read out in binning mode, frame transfer mode or other appropriate mode that will retain the ordinary and extraordinary polarization information. In general, CCD or CMOS array detectors and their use are well known by those skilled in the art. Alternatively, other photodetector arrays may be used if desired. Additionally, if desired charge injection devices (CID) or intensified CCD (iCCD) detectors may be useful, particularly if a pulsed light source is used.

Advantageously, with ellipsometer 400, both the ordinary polarized component and the extraordinary polarized component are simultaneously detected. Accordingly, reference data may be easily generated by summing the intensities of the ordinary and extraordinary polarization components. The spatial phase modulation of ordinary polarization component has a 180-degree phase difference from that of extraordinary polarization component. Thus, the sum of the two beams produces a total intensity Io in equation 2, which is invariant over the detector elements. The reference data may be used to correct for fluctuations in the light source 102 and non-uniformity of illumination across detector elements by normalizing Io in equation 2. Because the reference data can be easily generated at each measurement, the ellipsometer 400 can correct for both long term, as well as short term fluctuations. With the ability to correct for short term fluctuations, ellipsometer 400 may use high intensity lamps or pulsed light sources that typically have short term instabilities, such as Xenon lamps, flash lamps, metal halide lamps, and lasers.

In another embodiment, the ordinary and extraordinary polarized beams are processed at the same time and the polarization state information is extracted from both beams to increase the throughput of the system.

Without the use of beam splitter 402, a reference measurement must be made every few hours to correct any long term fluctuations in the light source. To generate a reference measurement, the variable retarder 118 is physically moved out of the beam path, the measurement taken, and the variable retarder 118 placed back in the beam path. Thus, the present invention is advantageous because it obviates the need to move the variable retarder 118 out of the beam path, and permits the system to be easily calibrated with every measurement.

In operation, the beam splitter 402 separates the phase shifted beam 120 into two separate beams that are orthogonally polarized. The device used to separate beam 120 into ordinary and extraordinary components may be, e.g., a displacer, such as the kind manufactured by Karl Lambrecht Corporation, located in Chicago, Ill. as part number BDA512. As shown in FIG. 13, aperture 403 is placed before the beam splitter 402 and the apertures 407 and 409 are placed before the detectors 408 and 410. The aperture 403 may be, e.g., 3 mm by 12 mm, and has the same size as apertures 407 and 409 to separate the two polarized beams. In one embodiment, a relay lens 405 (illustrated with broken lines) may be placed between polarizing beam splitter 402 before apertures 407 and 409 to focus the aperture 403 onto the detectors to reduce the aperture diffraction effect.

Figure 14:
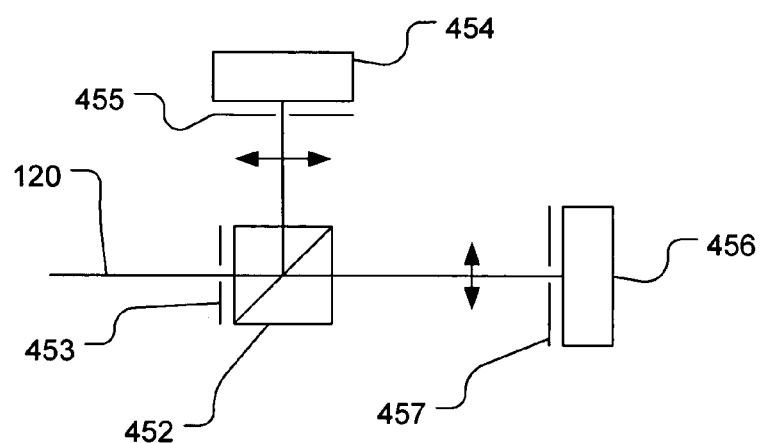
FIG. 14 shows one embodiment of a polarizing beam splitter that may be used in accordance with an embodiment of the present invention.

In another embodiment, a polarizing beam splitter may be used instead of a displacer, and two separate detectors are used. For example, a polarizing beam splitter such as part number MSBTA-12-45, manufactured by Karl Lambrecht Corporation, may be used. FIG. 14, by way of example, shows a polarizing beam splitter 452 that separates beam 120 into two orthogonally polarized beams that are incident on two physically separate detectors 454 and 456. As with the embodiment shown in FIG. 13, apertures 453, 455, and 457 are used with beam splitter 452 and detectors 454 and 456, respectively. It should be understood that the separation of the two beams can be at a variety of angles.

The detectors 408 and 410 are coupled to a processor 412 that receives signals from the detectors 408 and 410 indicative of the intensities of ordinary polarized and extraordinary polarized beams. The processor 412, which may be, e.g., a workstation, a personal computer, or central processing unit, e.g., Pentium 4™ or other adequate computer system, may include a computer-usable medium having computer-readable program code embodied therein for determining a sum of the beam intensities to generate the reference data which may be used to normalize the intensity Io in equation 2. Generating code to generate a correction ratio is well within the abilities of those skilled in the art in light of the present disclosure. If desired, the intensity summation can be accomplished by an electronic summing circuit. The calibration is performed, e.g., by normalizing the ordinary polarized beam using the summed intensity to minimize the spatial and temporal variation of intensity Io in equation 2.

Figure 15:
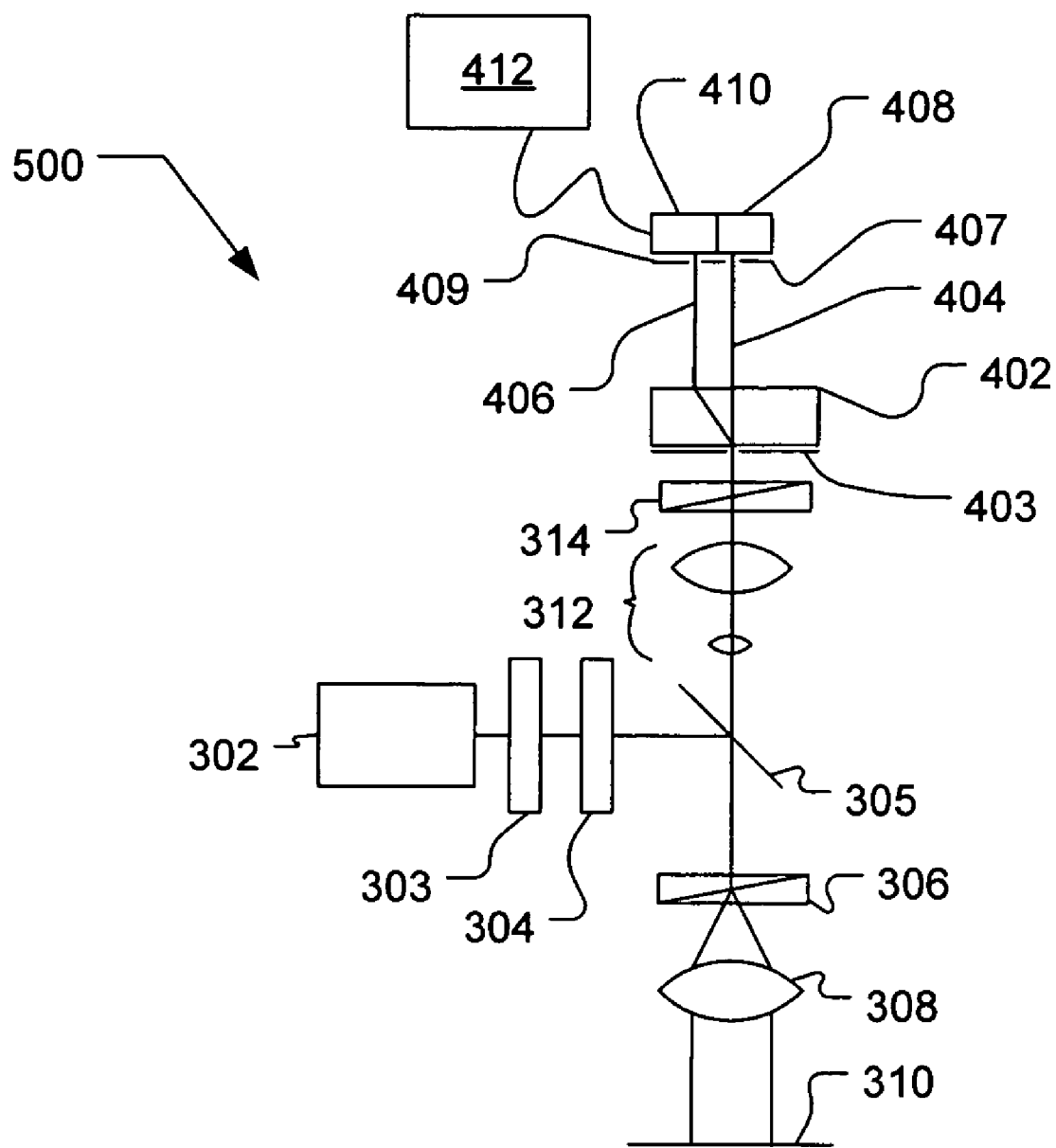
FIG. 15 illustrates an interferometer that includes a beam splitter.

It should be understood that while the beam splitter 402 is described in conjunction with an ellipsometer 400 that is similar to ellipsometer 100 shown in FIG. 3, the present invention may be used with other metrology configurations, such as with an interferometer that is similar to interferometer 300 shown in FIG. 12. FIG. 15 illustrates an interferometer 500 that includes a beam splitter 402. The beam splitter 402 operates in a manner similar to that described above. Of course, the beam splitter 452 shown in FIG. 14 may also be used with interferometer 500.

Although the present invention is illustrated in connection with specific embodiments for instructional purposes, the present invention is not limited thereto. Various adaptations and modifications may be made without departing from the scope of the invention. For example, the ellipsometer in accordance with the present invention may operate in either reflection or transmission mode. Further, it should be understood that the various components and configurations disclosed herein may be used with ellipsometer 400. For example, ellipsometer 400 may operate in spectroscopic mode with the use of appropriate filters in the paths of the separate beams 404 and 406. Further, the various types of components, such as variable retarders and expanders, may be used with ellipsometer 400. Therefore, the spirit and scope of the appended claims should not be limited to the foregoing description.

What is claimed is:

1. A metrology device comprising:
  a polarization state generator, including an electromagnetic source, the polarization state generator produces an electromagnetic beam of known polarization state that is incident on a sample;
  a spatial variable phase retarder in the path of the electromagnetic beam after the sample;
  a polarizing beam splitter in the path of the electromagnetic beam after the spatial variable phase retarder, the polarizing beam splitter splitting the electromagnetic beam into a first beam having a first polarization state and a second beam having a second polarization state that is orthogonal to the first polarization state; and
  a first set of detector elements within the path of the first beam after the polarizing beam splitter and a second set of detector elements within the path of the second beam after the polarizing beam splitter, wherein the first set of detector elements and the second set of detector elements measure the intensity of the first beam and second beam, respectively, as a function of position.

2. The metrology device of claim 1, further comprising a beam expander within the path of the electromagnetic beam before the spatial variable phase retarder.

3. The metrology device of claim 1, wherein the polarizing beam splitter is a displacer.

4. The metrology device of claim 1, further comprising:
  a first aperture before the polarizing beam splitter;
  a second aperture before the first set of detector elements; and
  a third aperture before the second set of detector elements.

5. The metrology device of claim 1, wherein the first set of detector elements and second set of detector elements are detector elements in a detector array.

6. The metrology device of claim 1, wherein the first set of detector elements and second set of detector elements are separate detectors.

7. The metrology device of claim 1, further comprising a means for summing the intensities of the first beam and the second beam.

8. The metrology device of claim 7, further comprising a means for normalizing the first and second polarizing beam using said summed intensities.

9. The metrology device of claim 8, wherein said means for summing the intensities and means for normalizing is a computer system coupled to the first set of detector elements and second set of detector elements, the computer system receiving signals indicative of the intensity of the first beam and the second beam, the computer system having a computer-usable medium having computer-readable program code embodied therein for:
  summing the intensities of the first beam and the second beam; and
  normalizing the first and second polarizing beam using said summed intensities.

10. The metrology device of claim 1, further comprising at least one relay lens disposed between the polarizing beam splitter and the first set of detector elements and the second set of detector elements.

11. A method of ellipsometrically measuring a sample, the method comprising:
  producing an electromagnetic beam to be incident on a sample;
  polarizing the electromagnetic beam prior to being incident on the sample;
  producing a spatially dependent relative phase difference between the electromagnetic field components of the electromagnetic beam after the beam is incident on the sample;
  splitting the electromagnetic beam after a spatially dependent relative phase difference is produced into two beams having orthogonal polarization states; and
  detecting the intensities of the two beams having orthogonal polarization states at a plurality of positions.

12. The method of claim 11, further comprising expanding the electromagnetic beam prior to producing a spatially dependent relative phase difference.

13. The method of claim 11, further comprising summing the intensities of the two beams having orthogonal polarization states.

14. The method of claim 13, further comprising using the summed intensities by normalizing the produced electromagnetic beam.

15. An apparatus for measuring a characteristic of a sample, the apparatus comprising:
  a light source producing an electromagnetic beam;
  a polarizer in the path of the electromagnetic beam, wherein the polarized electromagnetic beam is incident on the sample;
  means for producing a spatially dependent phase shift in the electromagnetic beam after the electromagnetic beam is incident on the sample, the means for producing a spatially dependent phase shift producing a phase shifted beam wherein the phase shift is spatially dependent;
  means for splitting the phase shifted beam into a first beam and a second beam, wherein the first beam and second beam are orthogonally polarized;
  means for measuring the intensity of the first beam and the second beam, the means for measuring being in the path of the first beam and the second beam; and
  means for summing the intensities of the first beam and the second beam.

16. The apparatus of claim 15, further comprising a means for expanding the electromagnetic beam, the means for expanding being in the path of the electromagnetic beam before the means for producing a spatially dependent phase shift.

17. The apparatus of claim 15, wherein the means for producing a spatially dependent phase shift comprises a spatial variable retarder.

18. The apparatus of claim 15, wherein the means for splitting the phase shifted beam into a first beam and a second beam comprises a displacer.

19. The apparatus of claim 15, wherein the means for splitting the phase shifted beam into a first beam and a second beam comprises a polarizing beam splitter.

20. The apparatus of claim 15, wherein the means for measuring the intensity of the first beam and the second beam comprises a first set of detectors that receive the first beam and a second set of detectors that receive the second beam.

21. The apparatus of claim 20, wherein the first set of detectors and the second set of detectors are elements in a detector array.

22. The apparatus of claim 20, wherein the first set of detectors and the second set of detectors are separate linear detectors.

23. The apparatus of claim 15, wherein the means for summing the intensities of the first beam and the second beam comprises a computer system coupled to the means for measuring the intensity of the first beam and the second beam, the computer system receiving signals indicative of the intensity of the first beam and the second beam, the computer system having a computer-usable medium having computer-readable program code embodied therein for summing the intensities of the first beam and the second beam.

24. The metrology device of claim 15, further comprising at least one relay lens disposed between the means for splitting the phase shifted beam and the means for measuring the intensity of the first beam and the second beam.

* * * * *